(12) United States Patent
Zhang et al.

(10) Patent No.: US 12,376,756 B2
(45) Date of Patent: Aug. 5, 2025

(54) ELECTRICAL IMPEDANCE TOMOGRAPHY APPARATUS AND METHOD

(71) Applicants: BEIJING HUARUI BOSHI MEDICAL IMAGING TECHNOLOGY CO., LTD., Beijing (CN); TSINGHUA UNIVERSITY, Beijing (CN)

(72) Inventors: Xin Zhang, Beijing (CN); Yibing Wang, Beijing (CN); Ke Zhang, Beijing (CN); Yang Yu, Beijing (CN)

(73) Assignees: BEIJING HUARUI BOSHI MEDICAL IMAGING TECHNOLOGY CO., LTD., Beijing (CN); TSINGHUA UNIVERSITY, Beijing (CN)

( * ) Notice: Subject to any disclaimer, the term of this patent is extended or adjusted under 35 U.S.C. 154(b) by 881 days.

(21) Appl. No.: 17/440,469

(22) PCT Filed: Jun. 19, 2019

(86) PCT No.: PCT/CN2019/091837
§ 371 (c)(1),
(2) Date: Sep. 17, 2021

(87) PCT Pub. No.: WO2020/199367
PCT Pub. Date: Oct. 8, 2020

(65) Prior Publication Data
US 2022/0160249 A1    May 26, 2022

(30) Foreign Application Priority Data
Apr. 2, 2019  (CN) .......................... 201910261647.2

(51) Int. Cl.
A61B 5/0536    (2021.01)
A61B 5/00      (2006.01)
G06T 15/00     (2011.01)

(52) U.S. Cl.
CPC .......... A61B 5/0536 (2013.01); A61B 5/6846 (2013.01); A61B 5/743 (2013.01);
(Continued)

(58) Field of Classification Search
CPC ..... A61B 5/0536; A61B 5/6846; A61B 5/743; A61B 2560/0223; A61B 2562/046; G06T 15/00; G06T 2210/41
See application file for complete search history.

(56) References Cited

U.S. PATENT DOCUMENTS 5,626,146 A      5/1997  Barber et al.
10,064,568 B2 *  9/2018  Baier-Löwenstein ....................... A61B 5/0813

(Continued)

FOREIGN PATENT DOCUMENTS

CN    103690166 A    4/2014
CN    104027112 A    9/2014
(Continued)

OTHER PUBLICATIONS

International Search Report, Application No. PCT/CN2019/091839, dated Dec. 27, 2019 in 4 pages.
(Continued)

*Primary Examiner* — Jason M Sims
*Assistant Examiner* — Kyle W. Kretzer
(74) *Attorney, Agent, or Firm* — Procopio, Cory, Hargreaves & Savitch LLP (57) ABSTRACT

An electrical impedance tomography apparatus (100) and method. The electrical impedance tomography apparatus (100) consists of a sensing module (101), a data acquisition
(Continued)

module (102), a communication module (103), a data processing module (104), an image display module (105) and a power supply module (106). The electrical impedance tomography apparatus (100) is applicable to medical imaging, can employ an in vivo electrode to perform multi-frequency-one-time excitation and measurement on a biological tissue under test and use a measured complex voltage signal to perform three-dimensional image reconstruction, and can simultaneously display ventilation and perfusion images in real time, thereby increasing an amount of acquired data, increasing the speed of data acquisition, increasing the sensitivity of a measurement signal to the conductivity of an in vivo tissue, and facilitating image analysis and comparison, disease detection and diagnosis.

8 Claims, 4 Drawing Sheets

(52) U.S. Cl.
CPC ...... *G06T 15/00* (2013.01); *A61B 2560/0223* (2013.01); *A61B 2562/046* (2013.01); *G06T 2210/41* (2013.01)

(56) References Cited

U.S. PATENT DOCUMENTS

| | | | | |
|---|---|---|---|---|
| 2002/0123694 | A1* | 9/2002 | Organ | A61B 5/0536 73/1.01 |
| 2008/0252304 | A1* | 10/2008 | Woo | A61B 5/0536 324/692 |
| 2012/0200302 | A1* | 8/2012 | Wang | A61B 5/0536 324/600 |
| 2016/0296171 | A1* | 10/2016 | Drori | A61B 5/1072 |
| 2018/0177430 | A1* | 6/2018 | De Limon | A61B 5/0537 |
| 2019/0200893 | A1* | 7/2019 | Grouchy | A61B 5/0044 |

FOREIGN PATENT DOCUMENTS

| | | |
|---|---|---|
| CN | 107320101 A | 11/2017 |
| CN | 109864712 A | 6/2019 |
| GB | 2 454 925 A | 5/2009 |
| JP | 5-329122 A | 12/1993 |
| JP | 2003-164446 A | 6/2003 |
| JP | 2008-532638 A | 8/2008 |
| JP | 2017-525477 A | 9/2017 |
| WO | 2018/093136 A1 | 5/2018 |

OTHER PUBLICATIONS

Japanese Office Action for the counterpart Japanese Application No. 2021-560385, dated Aug. 9, 2022., 3 pages.
Extended European Search Report received in EP Application No. 19923630.8, dated Nov. 29, 2022, in 8 pages.
Tong in Oh, et al.: "Multi-frequency EIT System with Radially Symmetric Architecture: KHU Mark1", Physiological Measurement, Institute of Physics Publishing, Bristol, GB, vol. 28, No. 7, Jul. 1, 2007 (Jul. 1, 2007), pp. SI83-SI96, XP020120799, ISSN: 0967-3334, DOI: 10.1088/0967-3334/28/7/S14.

* cited by examiner

ELECTRICAL IMPEDANCE TOMOGRAPHY APPARATUS AND METHOD

The present application is a US national stage application of international application no. PCT/CN2019/091837 filed Jun. 19, 2019, which claims the priority of Chinese Invention patent Application No. 201910261647.2, entitled "Electrical Impedance Tomography Apparatus and Method" and filed on Apr. 2, 2019, the contents of each of which are incorporated by reference.

TECHNICAL FIELD

The present invention relates to an electrical impedance tomography technology, and in particular to a three-dimensional multi-frequency-one-time complex electrical impedance tomography apparatus and method applied to medical imaging.

BACKGROUND

Electrical Impedance Tomography (EIT) is a non-invasive technology for reconstructing images of an in vivo tissue with resistivity distribution inside the human body or other living bodies as a target. The human body is a large biological electric conductor, and each tissue and each organ have certain impedances; when a local organ of the human body is diseased, the local part certainly has a different impedance from other parts, therefore the disease of the human organ may be diagnosed by the impedance measurement.

Current electrical impedance tomography apparatus acquires data through in vitro electrodes; that is, the electrodes are all arranged on the outer surface of to-be-tested parts of the human body. A signal thus acquired is not sensitive to an electrical inhomogeneity in the living body. Therefore, an EIT image reconstruction problem is often a serious ill-conditioned one. Actual measurement data often contains noise, and a forward model used for image reconstruction often has errors, which causes that the reconstructed image contains artifacts. These artifacts may even obscure the real target, making subsequent image interpretation and medical mining work difficult.

In the process of the data acquisition, in the current electrical impedance tomography apparatus, excitation is performed through a constant current source, and then, a generated voltage signal is measured. After the measurement of the generated voltage signal, the constant current source of the electrical impedance tomography apparatus is switched to a next position for excitation. When a large number of electrodes are provided, the position of the constant current source is required to be switched for many times, which limits the data acquisition speed to a certain extent, and is not favorable for real-time image reconstruction.

In an imaging stage, the differential imaging is adopted in the current electrical impedance tomography apparatus, and the reconstructed image reflects a change of electrical properties of the human tissue between two moments or two frequencies. However, in practical applications, the electrical properties of biological tissue quantification often contain important medical information which is not available in a differential image.

An image displayed by the current electrical impedance tomography apparatus is a two-dimensional one which reflects the conductivity or the dielectric constant of a certain section of the human tissue. However, the two-dimensional image cannot reflect three-dimensional structural information of the biological tissue or organ, which causes inconvenience in the detection and diagnosis of diseases.

Furthermore, the current electrical impedance tomography apparatus displays either only a ventilation image of the lungs or one of ventilation and perfusion images of the lungs alone, and cannot display the ventilation and perfusion images of the lungs simultaneously. In practical applications, synchronous analysis of the ventilation and perfusion images of the lungs is of a great medical significance.

Therefore, it is desirable to provide an electrical impedance tomography apparatus and method, which are applicable to the medical field; multi-frequency-one-time excitation and measurement are performed on the to-be-tested biological tissue, and three-dimensional image reconstruction is performed with a measured complex voltage signal, thereby qualitatively or quantitatively measuring properties of the biological tissue, such as the conductivity or the dielectric constant.

SUMMARY

As mentioned above, in order to solve the problems in the prior art, an objective of the present invention is to provide a three-dimensional multi-frequency-one-time complex electrical impedance tomography medical apparatus, in which multi-frequency-one-time excitation and measurement are performed on the to-be-tested biological tissue, and three-dimensional image reconstruction is performed using a measured complex voltage signal, thereby qualitatively or quantitatively measuring properties of the biological tissue, such as the conductivity or the dielectric constant.

According to an embodiment of the present invention, a first aspect of the present invention provides an electrical impedance tomography apparatus. The electrical impedance tomography apparatus may include: a sensing module fixed around a measured part of the human body in an electrode array; a data acquisition module used for applying a constant current excitation signal to the sensing module and measuring a complex voltage signal on the electrode array in the sensing module; a communication module used for transmitting the complex voltage signal acquired by the data acquisition module to a data processing module and transmitting a control command of the data processing module to the data acquisition module; the data processing module used for processing the complex voltage signal acquired by the data acquisition module and performing image reconstruction; an image display module used for displaying the calculation result and the image generated by the data processing module; and a power supply module used for supplying power to the above-mentioned modules.

In the electrical impedance tomography apparatus according to the first aspect of the present invention, preferably, the electrode array may include at least 16 electrodes. The electrode array may include an in vivo electrode placed in the human body.

In the electrical impedance tomography apparatus according to the first aspect of the present invention, preferably, the data acquisition module may further include a constant current source, and optical isolation is adopted among the constant current sources in different data acquisition modules performing excitation simultaneously.

In the electrical impedance tomography apparatus according to the first aspect of the present invention, preferably, the data acquisition module may further include: a constant current source used for simultaneously applying excitation currents with a plurality of frequency components; a voltmeter used for simultaneously measuring complex voltage signals with a plurality of frequencies; a switch array including several analog switches and used for turning on and off the application of the excitation currents and the measurement of the complex voltage signals; a control logic circuit used for controlling the switches in the switch array and the switching between the constant current source and the voltmeter; a multi-channel passage used for transmitting the excitation currents to the sensing module and receiving the complex voltage signals from the sensing module. The complex voltage signals may be expressed in terms of an amplitude and a phase, or real and imaginary parts.

In the electrical impedance tomography apparatus according to the first aspect of the present invention, preferably, the data processing module may have a three-dimensional image reconstruction function, and the image display module may display a three-dimensional reconstructed image.

In the electrical impedance tomography apparatus according to the first aspect of the present invention, preferably, the image display module may simultaneously display ventilation and perfusion images in real time.

Preferably, the electrical impedance tomography apparatus according to the first aspect of the present invention may further include a calibration disk formed by a resistive device and used for calibrating the systematic error and the distribution parameter of the apparatus.

According to an embodiment of the present invention, a second aspect of the present invention provides an electrical impedance tomography method. The electrical impedance tomography method may include the following steps: applying a constant current excitation signal to a measured part of the human body, and measuring a complex voltage signal on the measured part; processing the complex voltage signal and performing image reconstruction according to a control command; and displaying the calculation result of processing the complex voltage signal and the reconstructed image.

According to an embodiment of the present invention, a third aspect of the present invention provides a computer readable medium. The computer readable medium according to the third aspect of the present invention may be used for recording instructions executable by a processor, the instructions, when executed by the processor, cause the processor to perform the electrical impedance tomography method including the following operations: applying a constant current excitation signal to a measured part of the human body, and measuring a complex voltage signal on the measured part; processing the complex voltage signal and performing image reconstruction according to a control command; and displaying the calculation result of processing the complex voltage signal and the reconstructed image.

The electrical impedance tomography apparatus according to the embodiment of the present invention is applicable to medical imaging, can employ the in vivo electrode to perform the multi-frequency-one-time excitation and measurement on the to-be-tested biological tissue and adopt the measured complex voltage signal to perform the three-dimensional image reconstruction, and can simultaneously display the ventilation and perfusion images in real time, thereby increasing an amount of acquired data, increasing the speed of data acquisition, increasing the sensitivity of a measurement signal to the conductivity of an in vivo tissue, and facilitating image analysis and comparison, as well as disease detection and diagnosis.

BRIEF DESCRIPTION OF THE DRAWINGS

Hereinafter, the present invention will be described with reference to the drawings in combination with the embodiments.

DETAILED DESCRIPTION

The drawings are only for purposes of illustration and are not to be construed as limiting the present invention. The technical solution of the present invention is further described below with reference to the drawings and the embodiments.

Figure 1:
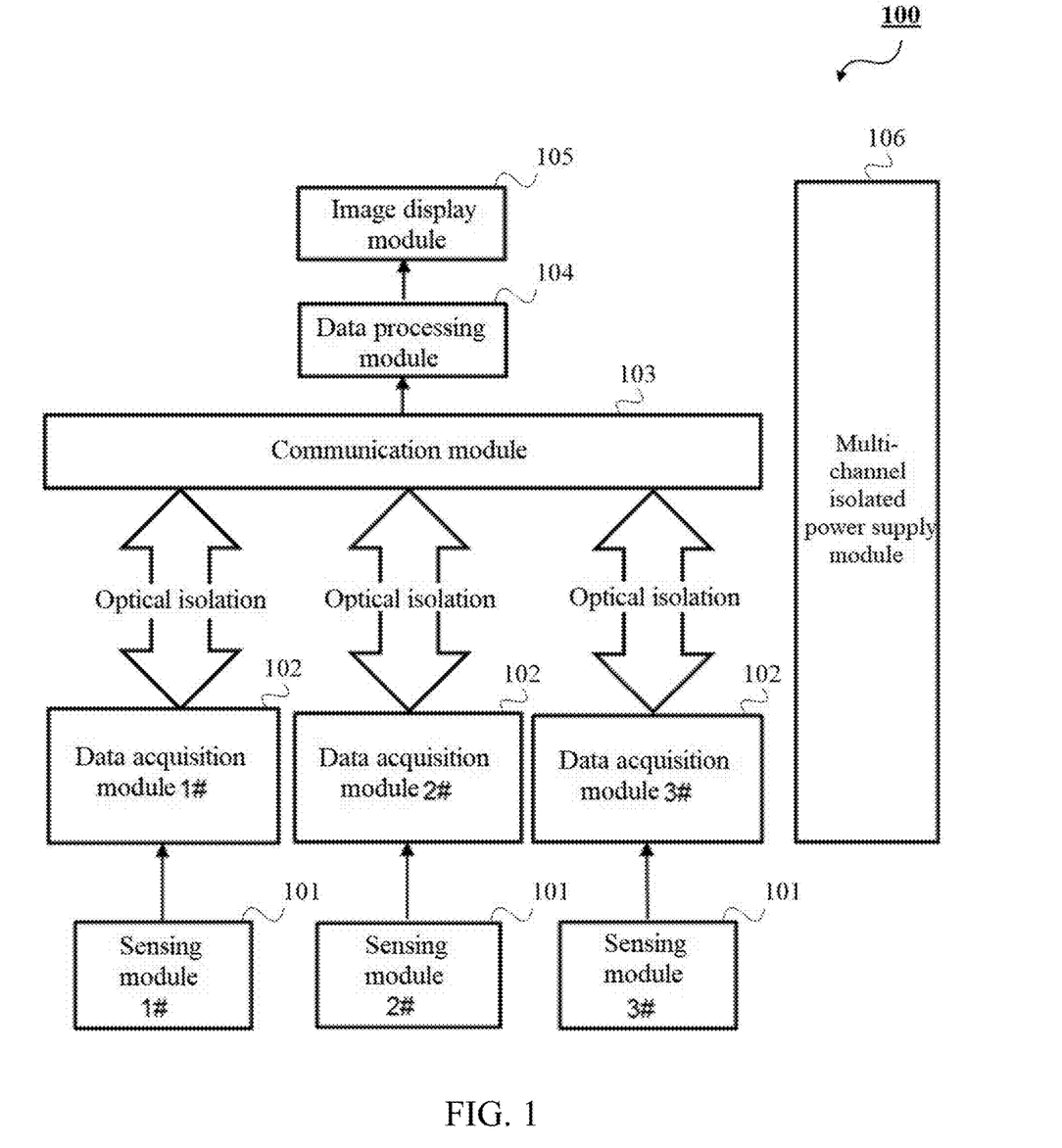
FIG. 1 is a composition block diagram illustrating an electrical impedance tomography apparatus according to an embodiment of the present invention.

FIG. 1 is a composition block diagram illustrating an electrical impedance tomography apparatus 100 according to the embodiment of the present invention.

As shown in FIG. 1, the electrical impedance tomography apparatus 100 according to the embodiment of the present invention is generally composed of a sensing module 101, a data acquisition module 102, a communication module 103, a data processing module 104, an image display module 105, and a power supply module 106. Among them, the sensing module 101 and the data acquisition module 102 are optically isolated from the communication module 103, the data processing module 104, the image display module 105 and the power supply module 106 electrically.

The sensing module 101 is fixed around a measured part of the human body, such as the thoracic cavity, the brain, the abdomen or the limbs, and takes the form of an electrode array, such as an impedance strip, an electrode vest, or the like. According to a preferred embodiment of the present invention, each sensing module includes at least 16 electrodes. Moreover, in the preferred embodiment of the present invention, the electrode may take the form of an in vivo electrode. The so-called in vivo electrode refers to an electrode placed at positions in the human body, such as the esophagus, the trachea, or the like. The electrical impedance tomography apparatus according to the embodiment of the present invention may include a plurality of sensing modules 101. In FIG. 1, three sensing modules are shown, which are sensing module 1 #, sensing module 2 #, and sensing module 3 #, respectively. It should be understood by those skilled in the art that the drawings are only schematic, the number of the sensing modules in practice is not limited to three, and may be more or less, and the sensing modules are collectively referred to as the sensing module, and all may be denoted by 101.

The data acquisition module 102 is used for applying a constant current excitation signal to the sensing module 101 and measuring a complex voltage signal on the electrode array in the sensing module 101. The complex voltage signal may be expressed in terms of an amplitude and a phase, or real and imaginary parts. In FIG. 1, three data acquisition modules are shown: data acquisition module 1 #, data acquisition module 2 #and data acquisition module 3 #, which correspond to the sensing module 1 #, the sensing module 2 #and the sensing module 3 #, respectively. It should be understood by those skilled in the art that the drawings are only schematic, the number of the data acquisition modules in practice is not limited to three, and may be more or less, and the data acquisition modules are collectively referred to as the data acquisition module, and all may be denoted by 102.

Figure 2:
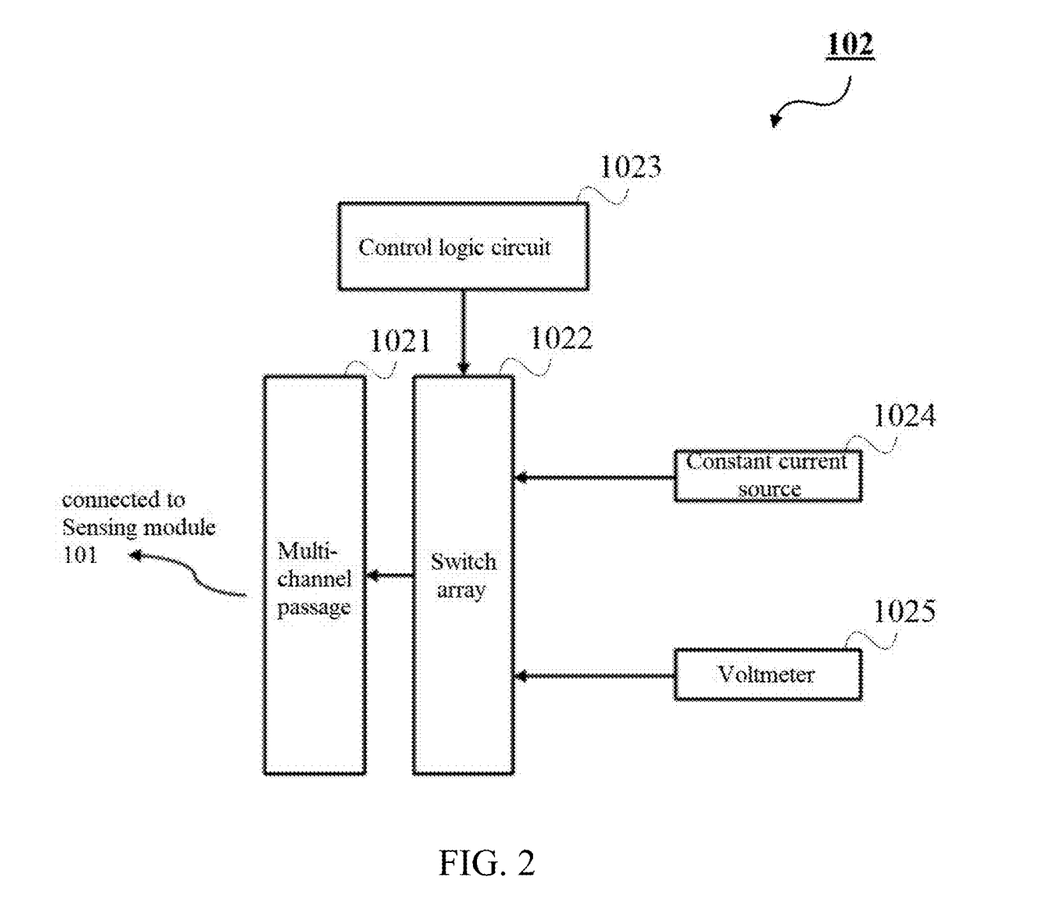
FIG. 2 is a composition block diagram illustrating the data acquisition module of the electrical impedance tomography apparatus according to the embodiment of the present invention.

FIG. 2 is a composition block diagram illustrating the data acquisition module 102 of the electrical impedance tomography apparatus 100 according to the embodiment of the present invention. As shown in FIG. 2, the data acquisition module 102 includes a multi-channel passage 1021, a switch array 1022, a control logic circuit 1023, a constant current source 1024, and a voltmeter 1025. The multi-channel passage 1021 is used for transmitting an excitation current to the sensing module 101 and receiving the complex voltage signal from the sensing module 101. The switch array 1022 includes several analog switches and is used for turning on and off the application of the excitation current and the measurement of the complex voltage signal. The control logic circuit 1023 is used for controlling the switches in the switch array 1022 and the switching between the constant current source 1024 and the voltmeter 1025, and may be implemented by a Field Programmable Gate Array (FPGA). In order to increase the rate of data acquisition, simultaneous excitation may be performed by the constant current sources (not shown in FIG. 1) in different data acquisition modules (for example, the data acquisition module 1 #, the data acquisition module 2 #, and the data acquisition module 3 #). In order to avoid danger of a short circuit in the human body caused by a plurality of zero potentials that are generated on the human body when the human body is excited simultaneously, optical isolation is adopted among the constant current sources for simultaneous excitation. In addition, in order to utilize the response characteristic of a biological tissue to a signal frequency, a multi-frequency-one-time excitation and measurement method is adopted. Specifically, the constant current source 1024 in FIG. 2 may simultaneously apply the excitation currents with a plurality of frequency components, and the voltmeter 1025 may correspondingly measure the complex voltage signals with a plurality of frequencies simultaneously.

Returning to FIG. 1, the communication module 103 is used for transmitting voltage data (the complex voltage signal) acquired by the data acquisition module 102 to the data processing module 104, and may also transmit a control command of the data processing module 104 to the data acquisition module 102. The communication module 103 may take the form of a serial interface circuit. Optical isolation is adopted between the communication module 103 and the data acquisition module 102.

The data processing module 104 is used for processing the complex voltage signal acquired by the data acquisition module 102 and performing image reconstruction. The module 104 may be an apparatus with an operation function, such as a computer, or the like, and a corresponding computer program. The module 104 uses a signal processing method to detect whether a measurement or excitation range is exceeded and detect situations of poor electrode contact or electrode detachment. The module 104 has a three-dimensional image reconstruction function. Conventionally, the module 104 may perform differential imaging with time domain differentiation or frequency domain differentiation. The so-called differential imaging means that the reconstruction is performed with the difference between measured data at two moments or two frequency components, and the reconstructed image reflects an amount of change in the conductivity or the dielectric constant of a biological tissue between the two moments or the two frequency components.

The module 104 may also perform direct imaging. The so-called direct imaging specifically means that the reconstructed image reflects an absolute value of the conductivity or the dielectric constant of the biological tissue.

The image display module 105 is used for displaying the calculation result and the image generated by the data processing module. The module 105 may be a displayer. In a preferred embodiment, corresponding to the data processing module 104 with a three-dimensional image reconstruction function, the image display module 105 may display a three-dimensional reconstructed image. Further, in a preferred embodiment of the present invention, the image display module 105 may simultaneously display ventilation and perfusion images in real time.

Figure 3:
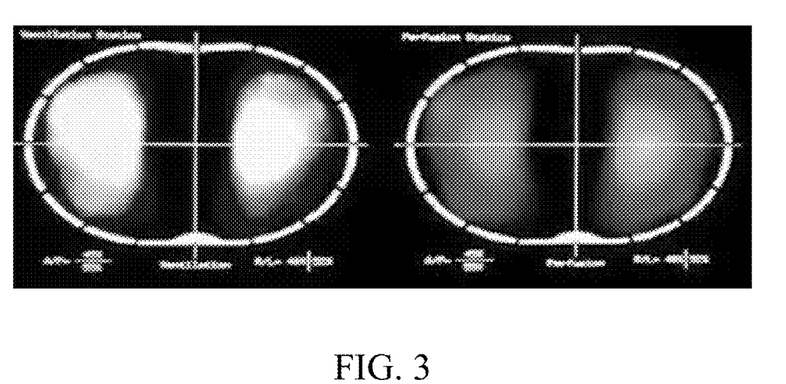
FIG. 3 is a schematic diagram illustrating ventilation and perfusion images displayed by the image display module of the electrical impedance tomography apparatus according to the embodiment of the present invention.

FIG. 3 is a schematic diagram illustrating the ventilation and perfusion images displayed by the image display module of the electrical impedance tomography apparatus according to the embodiment of the present invention.

In FIG. 3, a ventilation image of the lungs is shown on the left side, and a blood perfusion image of the lungs is shown on the right side. A reconstruction process of the ventilation image of the lungs includes: first extracting ventilation signals from measured data, and then performing image reconstruction with the difference of the ventilation signals at different moments. Similarly, a reconstruction process of the blood perfusion image of the lungs includes: first extracting perfusion signals from measured data, and then performing image reconstruction with the difference of the perfusion signals at different moments. Both the ventilation image of the lungs and the blood perfusion image of the lungs are images of the change in the conductivity. The ventilation image of the lungs reflects a change in gas content of the lungs at different moments. The blood perfusion image of the lungs reflects a change in blood content of the lungs at different moments. It will be appreciated by those skilled in the art that although a two-dimensional image screenshot is shown in FIG. 3, a three-dimensional image may be reconstructed and displayed in practice; that is, a three-dimensional ventilation image and a three-dimensional blood perfusion image may be simultaneously displayed in real time.

In addition, it will be appreciated by those skilled in the art that the power supply module 106 is used for supplying power to the sensing module 101, the data acquisition module 102, the communication module 103, the data processing module 104, and the image display module 105 described above.

Preferably, in the electrical impedance tomography apparatus according to the embodiment of the present invention, a calibration disk (not shown) may be formed by a resistive device and used for calibrating the systematic error and the distribution parameter of the apparatus.

Figure 4:
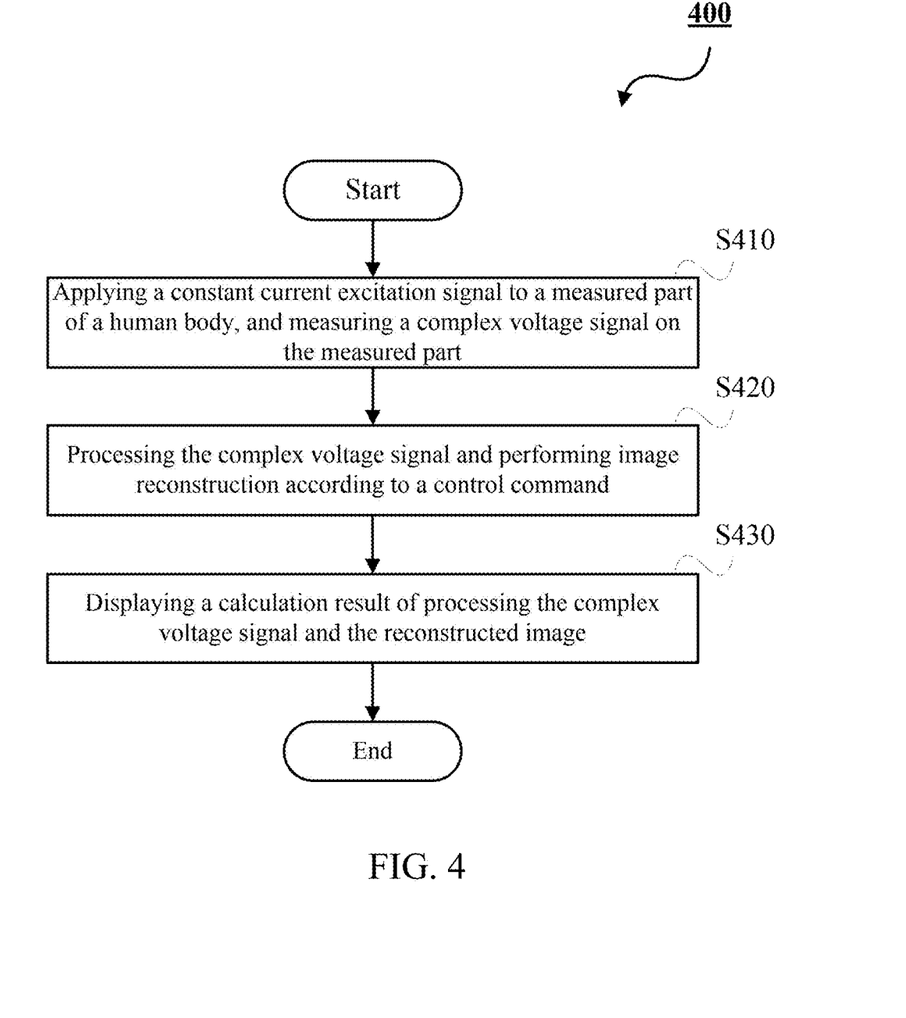
FIG. 4 is a flow chart of an electrical impedance tomography method according to an embodiment of the present invention.

FIG. 4 is a flow chart of an electrical impedance tomography method according to an embodiment of the present invention.

As shown in FIG. 4, the electrical impedance tomography method 400 according to the embodiment of the present invention starts with step S410. In step S410, a constant current excitation signal is applied to a measured part of the human body, and a complex voltage signal on the measured part is measured.

Referring to the previous description of the electrical impedance tomography apparatus, in the method 400, the constant current excitation signal is applied to the measured part of the human body by the data acquisition module (102 in FIG. 1) through the sensing module (101 in FIG. 1) in the form of the electrode array, and the complex voltage signal on the measured part reflected on the electrode array in the sensing module is measured.

The electrode array may include at least 16 electrodes. Moreover, the electrode array may include an in vivo electrode placed in the human body.

The data acquisition module further includes a constant current source, and optical isolation is adopted among the constant current sources in different data acquisition modules performing excitation simultaneously.

On the other hand, referring to the description of FIG. 2, within the data acquisition module, the constant current source (1024 in FIG. 2) is used for simultaneously applying excitation currents with a plurality of frequency components. The voltmeter (1025 in FIG. 2) is used for simultaneously measuring complex voltage signals with a plurality of frequencies. The switch array (1022 in FIG. 2) includes several analog switches and is used for turning on and off the application of the excitation currents and the measurement of the complex voltage signals. The control logic circuit (1023 in FIG. 2) is used for controlling the switches in the switch array and the switching between the constant current source and the voltmeter. The multi-channel passage (1021 in FIG. 2) is used for transmitting the excitation currents to the sensing module (101 in FIG. 1) and receiving the complex voltage signals from the sensing module. The complex voltage signals may be expressed in terms of an amplitude and a phase, or real and imaginary parts.

Next, in step S420, the complex voltage signal is processed and an image reconstruction is performed according to a control command.

Referring to the previous description of the electrical impedance tomography apparatus, in the method 400, since the data processing module (104 in FIG. 1) may have a three-dimensional image reconstruction function, the image reconstruction in step S420 may be three-dimensional image reconstruction.

In Step S430, the calculation result of processing the complex voltage signal and the reconstructed image is displayed.

Correspondingly, since the image reconstruction may be three-dimensional image reconstruction, the displayed reconstructed image may be a three-dimensional reconstructed image.

On the other hand, in step S430, both a differential image and a direct image may be displayed; that is, the reconstructed image may reflect an absolute value of the conductivity or the dielectric constant of a biological tissue.

In a preferred embodiment, step S430 of the method 400 has a more important feature that both ventilation and perfusion images may be simultaneously displayed in real time.

After step S430 is completed, the flow of the method 400 ends.

Furthermore, the method 400 may additionally include a calibration step of using a calibration disk formed by a resistive device for calibrating the systematic error and the distribution parameter of the electrical impedance tomography apparatus.

In addition to the above-mentioned method steps, it will also be understood by those skilled in the art that, corresponding to the above-mentioned electrical impedance tomography apparatus according to the present invention, the electrical impedance tomography method according to the present invention may further include steps or technical features listed below (some of which are mentioned above in the description of the method steps but listed again here for emphasis):

1. multi-frequency-one-time excitation and measurement: excitation currents including a plurality of frequency components are simultaneously applied to two or more electrodes, and voltage signals with a plurality of frequencies are simultaneously measured by a measuring electrode;
2. a measurement signal is a complex voltage signal, and the complex voltage signal is utilized for image reconstruction;
3. a signal processing method is used to detect whether a measurement or excitation range is exceeded and detect situations of poor electrode contact or electrode detachment;
4. data is acquired using an electrode array, such as an impedance strip, an electrode vest, or the like, the electrode array includes at least 16 electrodes;
5. an in vivo electrode may be used for data acquisition;
6. optical isolation is adopted among constant current sources for simultaneous excitation;
7. a sensing module and a data acquisition module are optically isolated from a communication module, a data processing module, an image display module and a power supply module electrically;
8. differential imaging is performed using the time domain difference;
9. differential imaging is performed using the frequency domain difference;
10. direct imaging may be performed;
11. a reconstructed and displayed image is a three-dimensional image;
12. the ventilation and perfusion images may be simultaneously displayed in real time in the apparatus; and
13. a calibration disk is formed by a resistive device to calibrate the systematic error and the distribution parameter of the apparatus.

The apparatus and method according to the present invention are compared with the prior art hereinafter to summarize the advantages of the present invention.

In the apparatus and method according to the present invention, multi-frequency-one-time excitation and measurement are used, which on one hand may utilize the response characteristic of the biological tissue to a signal frequency to increase the amount of the acquired data, on the other hand may greatly increase the speed of data acquisition.

In the apparatus and method according to the present invention, the situations of poor electrode contact or electrode detachment may be automatically detected utilizing signal processing, thereby taking corresponding measures.

The present invention has a prominent feature of using an in vivo electrode for data acquisition, which may greatly increase the sensitivity of a measurement signal to the conductivity of the internal tissues of the human body or living bodies, in particular the tissues in the thoracic cavity.

In the present invention, a plurality of constant current sources may be simultaneously used for excitation, so as to increase the speed of data acquisition.

In the apparatus and method according to the present invention, the sensing module and the data acquisition module are optically isolated from the communication module, the data processing module, the image display module and the power supply module electrically, thus greatly reducing electrical interference in the data acquisition process.

In the present invention, in addition to the differential imaging, the direct imaging may be performed, thereby quantitatively measuring the conductivity and the dielectric constant of the human tissue.

In the present invention, the three-dimensional image is reconstructed and displayed, and the three-dimensional structure of the human tissue or organ may be displayed, thereby more facilitating image analysis as well as disease detection and diagnosis.

The present invention has another prominent feature that the ventilation and perfusion images may be displayed simultaneously, thereby facilitating comparative analysis.

In addition, in the present invention, a calibration disk is formed by a resistive device to calibrate the systematic error and the distribution parameter of the apparatus, thereby greatly reducing the influence of the systematic error and the distribution parameter on the measured data.

It will be appreciated by those skilled in the art that the method according to the present invention may be implemented as a computer program. As mentioned above with reference to FIGS. 1, 2, and 3, the method according to the above-mentioned embodiment is performed by one or more programs, including instructions for a computer or processor to perform an algorithm described with reference to the drawings. These programs may be stored through various types of non-transitory computer readable media and provided to the computer or processor. The non-transitory computer readable media include various types of tangible storage media. Examples of the non-transitory computer readable media include a magnetic recording medium (such as a floppy disk, a magnetic tape, and a hard disk drive), a magneto-optical recording medium (such as a magneto-optical disk), a Compact Disc-Read-Only Memory (CD-ROM), a CD-R, a CD-R/W, and a semiconductor memory (such as a ROM, a programmable ROM (PROM), an erasable PROM (EPROM), a flash ROM, and a Random Access Memory (RAM)). Further, these programs may be provided to the computer through various types of transitory computer readable media. Examples of the transitory computer readable media include an electric signal, an optical signal, and an electromagnetic wave. The transitory computer readable media may be used for providing the program to the computer through a wired communication path, such as an electric wire and an optical fiber, or a wireless communication path.

Therefore, according to the present invention, it is also possible to propose a computer program or a computer readable medium used for recording instructions executable by a processor, the instructions, when executed by the processor, cause the processor to perform an electrical impedance tomography method including the following operations: applying a constant current excitation signal to a measured part of the human body, and measuring a complex voltage signal on the measured part; processing the complex voltage signal and performing image reconstruction according to a control command; and displaying the calculation result of processing the complex voltage signal and the reconstructed image.

Various embodiments and implementations of the present invention have been described above. However, the spirit and scope of the present invention are not limited thereto. Those skilled in the art will be able to devise more applications in accordance with the teachings of the present invention which are within the scope of the present invention.

That is, the above-mentioned embodiments of the present invention are merely examples for clearly illustrating the present invention and are not intended to limit the embodiments of the present invention. Other variations or modifications in different forms may be made by those skilled in the art on the basis of the above description. It is unnecessary and impossible to list all the embodiments here. Any modification, replacement or improvement made within the spirit and principle of the present invention should be included in the protection scope of the claims of the present invention.

The invention claimed is:

1. An electrical impedance tomography apparatus, comprising:
   a plurality of electrode arrays configured to be fixed around a measured part of a human body;
   a plurality of data acquisition circuits each corresponding to one of the plurality of electrode arrays respectively and configured for applying a constant current excitation signal to the corresponding electrode array and measuring a complex voltage signal in the corresponding electrode array;
   a communication interface configured for transmitting the complex voltage signal acquired by each data acquisition circuit to a data processor and transmitting a control command of the data processor to each data acquisition circuit;
   the data processor configured for processing the complex voltage signal acquired by each data acquisition circuit and performing image reconstruction;
   an image display configured for displaying a calculation result and an image generated by the data processor; and
   a power supply configured for supplying power to the apparatus,
   wherein each data acquisition circuit further comprises:
   a constant current source configured for simultaneously applying excitation currents with a plurality of frequency components;
   a voltmeter configured for simultaneously measuring complex voltage signals with a plurality of frequencies;
   a switch array comprising several analog switches and configured for turning on and off application of the excitation currents and the measurement of the complex voltage signals;
   a control logic circuit configured for controlling the switches in the switch array and the switching between the constant current source and the voltmeter; and
   a multi-channel passage configured for transmitting the excitation currents to the corresponding electrode array and receiving the complex voltage signals from the corresponding electrode array,
   wherein the complex voltage signals are expressed in terms of an amplitude and a phase, or real and imaginary parts, and
   wherein simultaneous excitation is performed by a plurality of the constant current sources in different circuits of the data acquisition circuits and optical isolation is adopted among the constant current sources for the simultaneous excitation.

2. The electrical impedance tomography apparatus according to claim 1, wherein each electrode array comprises at least 16 electrodes.

3. The electrical impedance tomography apparatus according to claim 1, wherein each electrode array comprises an in vivo electrode configured to be placed in the human body.

4. The electrical impedance tomography apparatus according to claim 1, wherein the data processor has a three-dimensional image reconstruction function, and the image display is configured to display a three-dimensional reconstructed image.

5. The electrical impedance tomography apparatus according to claim 1, wherein the image display is configured to simultaneously display ventilation and perfusion images in real time.

6. The electrical impedance tomography apparatus according to claim 1, further comprising a calibration disk formed by a resistive device and configured for calibrating a systematic error and a distribution parameter of the apparatus.

7. An electrical impedance tomography method, comprising the following steps:
   providing a plurality of electrode arrays fixed around a measured part of a human body and a plurality of data acquisition circuits each corresponding to one of the plurality of electrode arrays respectively:
   applying a constant current excitation signal from each data acquisition circuit to the corresponding electrode array, and measuring a complex voltage signal in the corresponding electrode array;
   processing the complex voltage signal and performing image reconstruction according to a control command; and
   displaying a calculation result of processing the complex voltage signal and the reconstructed image,
   wherein the step of applying the constant current excitation signal from each data acquisition circuit to the corresponding electrode array, and measuring the complex voltage signal in the corresponding electrode array further comprises:
   in each data acquisition circuit,
   simultaneously applying, by a constant current source, excitation currents with a plurality of frequency components;
   simultaneously measuring, by a voltmeter, complex voltage signals with a plurality of frequencies;
   turning on and off, by a switch array comprising several analog switches, application of the excitation currents and the measurement of the complex voltage signals;
   controlling, by a control logic circuit, the switches in the switch array and the switching between the constant current source and the voltmeter; and
   transmitting, by a multi-channel passage, the excitation currents to the corresponding electrode array and receiving the complex voltage signals from the corresponding electrode array,
   wherein the complex voltage signals are expressed in terms of an amplitude and a phase, or real and imaginary parts, and
   wherein simultaneous excitation is performed by a plurality of the constant current sources in different circuits of the data acquisition circuits and optical isolation is adopted among the constant current sources for the simultaneous excitation.

8. A computer readable medium used for recording instructions executable by a processor, the instructions, when executed by the processor, causing the processor to perform the electrical impedance tomography method according to claim 7.

* * * * *